(12) United States Patent
Stone et al.

(10) Patent No.: US 10,206,630 B2
(45) Date of Patent: Feb. 19, 2019

(54) SYSTEMS FOR AUTOMATIC ASSESSMENT OF FALL RISK

(71) Applicants: Erik E. Stone, Columbia, MO (US); Donald A. Viragh, St. Louis, MO (US); George Chronis, St. Louis, MO (US)

(72) Inventors: Erik E. Stone, Columbia, MO (US); Donald A. Viragh, St. Louis, MO (US); George Chronis, St. Louis, MO (US)

(73) Assignee: Foresite Healthcare, LLC, St. Louis, MO (US)

(*) Notice: Subject to any disclaimer, the term of this patent is extended or adjusted under 35 U.S.C. 154(b) by 0 days.

(21) Appl. No.: 15/248,810

(22) Filed: Aug. 26, 2016

(65) Prior Publication Data

US 2017/0055917 A1 Mar. 2, 2017

Related U.S. Application Data

(60) Provisional application No. 62/211,472, filed on Aug. 28, 2015.

(51) Int. Cl.
- *G08B 23/00* (2006.01)
- *A61B 5/00* (2006.01)
- *A61B 5/11* (2006.01)

(52) U.S. Cl.
CPC ............ *A61B 5/7275* (2013.01); *A61B 5/112* (2013.01); *A61B 5/1115* (2013.01);
(Continued)

(58) Field of Classification Search
CPC ..... A61B 5/7275; A61B 5/112; A61B 5/1115; A61B 5/1128; A61B 5/1116;
(Continued)

(56) References Cited

U.S. PATENT DOCUMENTS

| | | |
|---|---|---|
| 4,320,766 A | 3/1982 | Alihanka et al. |
| 5,097,841 A | 3/1992 | Moriuchi et al. |

(Continued)

FOREIGN PATENT DOCUMENTS

| | | |
|---|---|---|
| CN | 2394612 Y | 8/2000 |
| CN | 2477135 Y | 2/2002 |

(Continued)

OTHER PUBLICATIONS

Shin et al, "Automatic Ballistocardiogram (BCG) Beat Detection Using a Template Matching Approach," 30th Annual International IEEE Engineering in Medicine and Biology Society Conference, Vancouver, British Columbia, Canada, Aug. 20-24, 2008, 1144-1146, 3 pages.

(Continued)

*Primary Examiner* — Anh V La
(74) *Attorney, Agent, or Firm* — Lewis Rice LLC

(57) ABSTRACT

Systems and methods for the automatic assessment of a person's fall risk. The systems and methods utilize an objective standard and evaluation of a person's gait and stance, among other factors, to determine such person's current instantaneous likelihood of a fall, as well as such person's future fall risk. The systems and methods utilize machine observations and calculations to reduce or eliminate bias and the use of subjective assessment criteria.

16 Claims, 1 Drawing Sheet

(52) U.S. Cl.
CPC ........... *A61B 5/1116* (2013.01); *A61B 5/1128* (2013.01); *A61B 5/746* (2013.01); *A61B 2562/0247* (2013.01)

(58) Field of Classification Search
CPC ............ A61B 2562/0247; A61B 5/746; A61B 5/0002; A61B 5/002; A61B 5/11; A61B 5/6892; A61B 5/7282; A61B 5/1117; A61B 5/445; H04N 7/188; H04N 5/2252; G06T 7/80; G06F 19/3418; A61G 2203/36; G08B 21/0211; G08B 21/0461; G08B 21/0446
USPC ........ 340/573.1, 573.4, 573.7, 540; 600/300, 600/301
See application file for complete search history.

(56) References Cited

U.S. PATENT DOCUMENTS

| | | | |
|---|---|---|---|
| 5,309,921 | A | 5/1994 | Kisner et al. |
| 5,844,488 | A | 12/1998 | Musick |
| 6,002,994 | A | 12/1999 | Lane et al. |
| 6,915,008 | B2 | 7/2005 | Barman et al. |
| 7,420,472 | B2 | 9/2008 | Tran |
| 7,502,498 | B2 | 3/2009 | Wen et al. |
| 7,843,351 | B2 | 11/2010 | Bourne et al. |
| 8,547,236 | B2 * | 10/2013 | Gannot ................. A61B 5/1117 340/540 |
| 8,723,677 | B1 * | 5/2014 | Kiani .................... A61B 5/1115 340/573.1 |
| 2001/0020395 | A1 | 9/2001 | Hubbard, Jr. |
| 2003/0058111 | A1 | 3/2003 | Lee et al. |
| 2003/0059081 | A1 | 3/2003 | Trajkovic |
| 2003/0085992 | A1 | 5/2003 | Arpa et al. |
| 2004/0030531 | A1 | 2/2004 | Miller et al. |
| 2004/0119716 | A1 | 6/2004 | Park et al. |
| 2004/0228503 | A1 | 11/2004 | Cutler |
| 2005/0088515 | A1 | 4/2005 | Geng |
| 2005/0094879 | A1 | 5/2005 | Harville |
| 2005/0124864 | A1 | 6/2005 | Mack et al. |
| 2005/0190062 | A1 | 9/2005 | Sullivan et al. |
| 2006/0042409 | A1 | 3/2006 | Nemoto |
| 2006/0055543 | A1 | 3/2006 | Ganesh et al. |
| 2006/0152378 | A1 | 7/2006 | Lokhorst et al. |
| 2007/0003146 | A1 | 1/2007 | Ko et al. |
| 2007/0085690 | A1 | 4/2007 | Tran |
| 2007/0152837 | A1 | 7/2007 | Bischoff et al. |
| 2007/0262247 | A1 | 11/2007 | Becerra et al. |
| 2007/0263900 | A1 | 11/2007 | Medasani et al. |
| 2007/0268480 | A1 | 11/2007 | Kaye |
| 2008/0077020 | A1 | 3/2008 | Young et al. |
| 2008/0117060 | A1 | 5/2008 | Cuddihy et al. |
| 2008/0169931 | A1 | 7/2008 | Gentry et al. |
| 2009/0079559 | A1 | 3/2009 | Dishongh et al. |
| 2009/0079813 | A1 | 3/2009 | Hildreth |
| 2009/0089089 | A1 | 4/2009 | Jang et al. |
| 2009/0141124 | A1 | 6/2009 | Liu et al. |
| 2009/0178199 | A1 | 7/2009 | Brauers et al. |
| 2009/0243833 | A1 | 10/2009 | Huang et al. |
| 2010/0049095 | A1 | 2/2010 | Bunn et al. |
| 2010/0152546 | A1 * | 6/2010 | Behan .................. A61B 5/0002 600/301 |
| 2010/0163315 | A1 | 7/2010 | York et al. |
| 2010/0171622 | A1 | 7/2010 | Brauers et al. |
| 2010/0256512 | A1 | 10/2010 | Sullivan |
| 2010/0302043 | A1 | 12/2010 | Skubic et al. |
| 2010/0330543 | A1 | 12/2010 | Black et al. |
| 2011/0054330 | A1 | 3/2011 | Pfeiffer et al. |
| 2011/0087113 | A1 | 4/2011 | Mack et al. |
| 2011/0306844 | A1 | 12/2011 | Young |
| 2011/0308015 | A1 | 12/2011 | Newham |
| 2012/0019643 | A1 | 1/2012 | Gideon et al. |
| 2012/0053423 | A1 | 3/2012 | Kenalty et al. |
| 2012/0101411 | A1 | 4/2012 | Hausdorff et al. |
| 2012/0123279 | A1 | 5/2012 | Brueser et al. |
| 2012/0130202 | A1 | 5/2012 | Jain |
| 2012/0172681 | A1 | 7/2012 | Sun |
| 2012/0253201 | A1 | 10/2012 | Reinhold |
| 2013/0267791 | A1 * | 10/2013 | Halperin ................ A61B 5/002 600/300 |
| 2014/0022081 | A1 * | 1/2014 | Ribble ................... A61B 5/746 340/573.4 |
| 2014/0303460 | A1 | 10/2014 | Corley et al. |
| 2015/0164238 | A1 * | 6/2015 | Benson .................. A47C 31/00 340/540 |

FOREIGN PATENT DOCUMENTS

| | | |
|---|---|---|
| CN | 101499106 A | 8/2009 |
| CN | 101953740 A | 1/2011 |
| CN | 202101963 U | 1/2012 |
| DE | 10305289 A1 | 8/2004 |
| DE | 102008011142 A1 | 8/2009 |
| DE | 102008058781 A1 | 6/2010 |
| FR | 2865032 A1 | 7/2005 |
| GB | 2445760 A1 | 7/2008 |
| HR | P20041063 A | 6/2007 |
| JP | 2006288932 A | 10/2006 |
| NL | 8701288 | 1/1989 |
| WO | 2008048078 A1 | 4/2008 |
| WO | 2013033524 A2 | 3/2013 |
| WO | 2013058985 A1 | 4/2013 |
| WO | 2013066601 A1 | 5/2013 |

OTHER PUBLICATIONS

ProHeMon, Proactive Health Monitoring: Final report of the research project in the Academy of Finland Proactive computing research program, Feb. 3, 2006, Tampere University of Technology, Institute of Signal Processing and Tampere University Hospital, Department of Clinical Physiology, Web, Retrieved from: http://www.cs.tut.fi/~varri/prohemon/ profina4.com, 14 pages.

Heise et al., "Refinement and Evaluation of a Hydraulic Bed Sensor," 33rd Annual International Conference of the IEEE Engineering in Medicine and Biology Society, Boston, Massachusetts, USA, Aug. 30-Sep. 3, 2011, pp. 4356-4360, 5 pages.

Heise et al., "Monitoring Pulse and Respiration with a Non-Invasive Hydraulic Bed Sensor," 32nd Annual International Conference of the IEEE Engineering in Medicine and Biology Society, Buenos Aires, Argentina, Aug. 31-Sep. 4, 2010, pp. 2119-2123, 5 pages.

Mack et al., "Development and Preliminary Validation of Heart Rate and Breathing Rate Detection Using a Passive, Ballistocardiography-Based Sleep Monitoring System," IEEE Transactions on Information Technology in Biomedicine, vol. 13, No. 1, Jan. 2009, pp. 111-120, 10 pages.

Yang et al., "Development of a PVDF Piezopolymer Sensor for Unconstrained In-Sleep Cardiorespiratory Monitoring," Journal of Intelligent Material Systems and Structures, Mar. 2003, pp. 185-190, vol. 14.

Watanabe et al., "Noninvasive Measurement of Heartbeat, Respiration, Snoring and Body Movement of a Subject in Bed via Pneumatic Method," IEEE Transactions on Biomedical Engineering, vol. 52, No. 12, Dec. 2005, pp. 2100-2107, 8 pages.

Zhu et al., "Real-Time Monitoring of Respiration Rhythm and Pulse Rate During Sleep," IEEE Transactions on Biomedical Engineering, vol. 53, No. 12, Dec. 2006, pp. 2553-2563, 11 pages.

Rosales et al., "Exploring Passive Heartbeat Detection Using a Hydraulic Bed Sensor System," A Thesis presented to the Faculty of the Graduate School University of Missouri-Columbia, Columbia, Missouri, USA, Dec. 2011, pp. 1-172, 172 pages.

Rosales et al., "Heartbeat Detection from a Hydraulic Bed Sensor Using a Clustering Approach," 34th Annual International Conference of the IEEE Engineering in Medicine and Biology Society, San Diego, California, USA, Aug. 28-Sep. 1, 2012, pp. 2383-2387, 5 pages.

Martin et al., "Gait Initiation in Community-Dwelling Adults with Parkinson Disease: Comparison with Older and Younger Adults

(56) References Cited

OTHER PUBLICATIONS without the Disease," Physical Therapy, Jun. 2002, vol. 82, No. 6, pp. 566-577 from www.physther.org, 12 pages.
Wall et al., "The Timed Get-up-and-go Test Revisited: Measurement of the Component Tasks," Department of Veterans Affairs, Journal of Rehabilitation Research and Development, vol. 37, No. 1, Jan./Feb. 2000, pp. 109-114, 5 pages.
Yaguchi et al., "Arbitrary Viewpoint Video Synthesis from Multiple Uncalibrated Cameras," IEEE Transactions on Systems, Man, and Cybernetics—Part B: Cybernetics, vol. 34, No. 1, Feb. 2004, pp. 430-439, 10 pages.
Anderson et al., "Recognizing Falls from Silhouettes," Proceedings of the 28th IEEE, Engineering in Medicine and Biology Society Annual International Conference, New York City, USA, Aug. 30-Sep. 3, 2006, 4 pages.
Davis et al., "Toward 3-D Gesture Recognition," Research supported by the National Science Foundation grants CDA-9200369, IRI-9122006 and IRI-9220768, Feb. 2004, 16 pages.
Harvey et al., "Speedup of Fuzzy Logic through Stream Processing on Graphics Processing Units," In Proceedings: IEEE Congress on Evolutionary Computation, 2008, pp. 3809-3814, 7 pages.
Sledge et al., "Emergent Trend Detection in Diurnal Activity," 30th Annual International IEEE Engineering in Medicine and Biology Society Conference, Vancouver, British Columbia, Canada, Aug. 20-24, 2008, pp. 3815-3818, 4 pages.
Bujnoch, Zachary, "Video Games and Healthcare: Bridging the Gap between Patient and Consumer," Mastering the Art & Science of Patient Adherence, Dec. 19, 2011, 3 pages.

\* cited by examiner

SYSTEMS FOR AUTOMATIC ASSESSMENT OF FALL RISK

CROSS REFERENCE TO RELATED APPLICATIONS

This application claims benefit of U.S. Provisional Patent Application No. 62/211,472, filed Aug. 28, 2015, the entire disclosure of which is herein incorporated by reference.

BACKGROUND OF THE INVENTION

1. Field of the Invention

This disclosure relates to systems for automatically assessing the likelihood that an individual observed by the system will suffer a fall while they are within a particular environment. Generally, the system will be used to assess the likelihood of a patient falling while in long term care or hospitalized.

2. Description of the Related Art

Watching a toddler learn to walk, one may find it difficult to believe that falling can be one of the most dangerous things that can happen to a human being. While children are known to fall down on what seems to be a near constant basis and generally jump right back up, as one ages the potential damage from a fall can go up dramatically.

When people discuss fall risk and the dangers of tails, they are generally talking about the risks for the elderly, which is a term commonly used to refer to those over age 65. That population is often much more susceptible to body damage from a fall and is more likely to suffer from falls as well. This population can be prone to increased falls from a myriad of problems such as worsening eyesight (e.g. due to issues such as presbyopia), decreases in muscle mass and reduced strength, and from taking medications which may induce dizziness or vertigo. Further this population is often more susceptible to damage from falls due to weakening of bones and lack of musculature which means that an impact from a fall is more likely to do more serious damage.

Falls in the elderly can be a substantial problem. It has been estimated that falls are the leading cause of both fatal and nonfatal injuries in the elderly and are one of the primary causes of broken bones (particularly hips) and head trauma. It has been estimated that 33% of the elderly will fall every year and that a third of those who fall will suffer moderate to severe injuries (or even death) because of the fall. This means that those who house or serve the elderly on a regular basis need to be constantly vigilant for the potential for falls.

Even outside of concerns about the elderly, falls can still present a major concern. This is particularly true in medical and hospital settings, in these settings, even normally able-bodied people can be susceptible to a dramatically increased risk of falls and the elderly (who often require more medical attention) can be particularly susceptible. Treatments and medications (most notably anesthetics and pain killers) used in medical settings can make patients dizzy, nauseous, or confused leading to them having a greatly heightened risk of falls. Further, injuries or symptoms which sent the person to the hospital in the first place (for example muscle weakness, damaged bones, or pain) can make a patient more susceptible to falls as well.

The susceptibility of the patient population to falls is also combined with institutional issues with hospitals and other medical facilities which can increase full risk and severity. Hospitals often have smooth surfaced, and very hard, floors for easy cleaning and disinfection, but this can also make them slippery. Further, hospital equipment is often bulky, but needs to be placed in close proximity to patient areas to make it accessible quickly which can reduce open areas and require more complicated navigation. Finally, since a hospital is generally a foreign environment to the patient, they are also susceptible to simple lack of familiarity and can misestimate the size and shape of steps or pathways resulting in a fall.

Falls for hospitalized patients are believed to present 30-40% of safety incidents within any hospital and will generally occur at a rate of 4-14 for every 1000 bed days at a hospital. For even a relatively small facility, this can lead to multiple fall incidents every month, and can make them a near daily occurrence for a large institution. The problem is exacerbated because falls are often seen as a preventable and, therefore, while they are very common injuries (and in some cases likely unavoidable), falls can result in punishment to the hospital in the form of reduced governmental recognition for quality of care and malpractice lawsuits.

To try and reduce the risk and severity of falls in the hospital setting, and in facilities such as nursing and retirement homes with a predominantly elderly population, many facilities utilize a variety of fall risk assessment tools to try and determine a risk factor for a particular patient to fall while they are within the facility. In most cases, these relate to a patient's answers on various forms of questionnaire and observations of facility personnel on the behavior of the patient. These systems are known to suffer from a myriad of problems.

In the first instance, most current fall risk assessments are subjective and may rely on flawed perceptions about the person's risk of a fall. Secondly, they are often assessed only on certain known risks. For example, a person may be known to be a fall risk because they have recently been under general anesthesia, a risk factor that can unquestionably result in increased fall risk. However, individuals tend to react differently to anesthesia, and, therefore, it can be difficult to assess when a person's likelihood of fall has decreased to an acceptable level as the anesthesia wears off which can result in a miscalculation of fall risk.

Because of these problems, assessment of fall risk tends to result in multiple problems in the hospital setting. The first of these is that the likelihood of fall is often greatly over calculated forcing those without any real risk to have to be in wheelchairs, or confined to bed, when there is no need for it. A second problem is that actual falls have been found to only be reduced by a mere 20% using current methods. Part of the reason for such problems is that the calculations of fall risk are often not quick to perform and are subjective as discussed above.

It can be difficult to determine a person's fall risk, for example, shortly after they arrive at the institution as they may not have had the chance to answer survey questions (or may be unable to, for example due to a language harrier) and personnel may not have had a chance to observe them. Further, even if fall risk can be determined relatively quickly, general condemnation of falls can still result in hospitals taking overly restrictive corrective measures in the first instance. These themselves can cause those who think they are being improperly confined to take risks they should not because they see the system as being overly inclusive.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein is a system and method for the automatic assessment of a person's fall risk. The systems and methods herein utilize a more objective standard and evaluation of a person's gait and stance and other factors to determine their current, and instantaneous, likelihood of a fall as well as their ongoing fall risk. Further the systems and methods used herein utilize machine observations and calculations so as to eliminate much of the potential bias or relative skill that is currently used in conjunction with human observations and evaluations.

Described herein, among other things, is a method of assessing the risk of a human being falling, comprising: providing a central sever system; providing a plurality of sensors communicatively coupled to the central server system, none of the sensors being in physical contact with the human being; receiving at the central server system from the plurality of sensors data about the human being gathered by the plurality of sensors; the central server system extracting from the received data about the human being a plurality of data features; the central server system determining a fall risk for the human being based at least in part on the extracted data features.

In an embodiment of the method, each sensor in the plurality of sensors is selected from the group consisting of a depth sensor, a bed sensor, and a pressure map sensor.

In another embodiment of the method, at least one sensor in the plurality of sensors is a depth sensor, and the depth sensor is an infrared camera.

In another embodiment of the method, at least one extracted data features in the plurality of extracted data features is selected from the group consisting of: bed exit procedure, sit-to-stand time, gait, duration of bed occupancy, whether the human being is undergoing intravenous therapy, and whether the human being is using an assisting device.

In another embodiment of the method, the method steps are performed after: at least one sensor in the plurality of sensors detecting the human being attempting to exit a bed in which the human being is resting; receiving at the central server system from the at least one sensor an indication of the detected attempt of the human being to exit the bed; wherein the extracted data features comprise bed exit procedure and sit-to-stand time.

In another embodiment of the method, the method further comprises: providing an electronic medical records database communicatively coupled to the central computer server; the central server system identifying in the electronic medical records database an electronic medical record for the human being, the identifying based at least in part on the extracted data features; in the determining step, the central server system determining the fall risk for the human being further based at least in part on medical information about the human being in the identified electronic medical record.

In another embodiment of the method, the method further comprises: the central server system causing to be stored a non-transitory computer-readable medium a data record of the plurality extracted features and the determined fall risk.

In another embodiment of the method, the method further comprises: receiving at the central server system from the plurality of sensors additional data about the human being gathered by the plurality of sensors; the central server system extracting from the received additional data about the human being a second plurality of data features; the central server system determining a second fall risk for the human being based at least in part on the second extracted data features, and at least in part on the extracted data features in the data record of the non-transitory computer readable medium.

In another embodiment of the method, the method further comprises: providing a monitoring computer system communicatively coupled to the central computer server; the central computer server transmitting to the monitoring computer system an indication of the determined fall risk; the monitoring computer system displaying the transmitted indication of the determined fall risk.

In another embodiment of the method, the monitoring computer system is a desktop computer system of a nurse station in a medical facility.

In another embodiment of the method, the monitoring computer is a mobile device.

In another embodiment of the method, the method further comprises: if the determined fall risk is above a predefined threshold, the central computer server causing a fall risk alert to be provided to the human being.

Also described herein, among other things, is a system for assessing the risk of a human being falling, comprising: a plurality of sensors, none of the sensors being in physical contact with the human being; a central sever system communicatively coupled to the plurality of sensors, the central server system comprising a microprocessor and a non-transitory computer-readable medium having computer-executable program instructions thereon which. When executed by the microprocessor, cause the central server to perform the steps of: receiving from the plurality of sensors data about the human being gathered by the plurality of sensors; extracting from the received data about the human being a plurality of data features; determining a fall risk for the human being based at least in part on the extracted data features.

In an embodiment of the system, each sensor in the plurality of sensors is selected from the group consisting of: a depth sensor, a bed sensor, and a pressure map sensor.

In another embodiment of the system, at least one sensor in the plurality of sensors is a depth sensor, and the depth sensor is an infrared camera.

In another embodiment of the system, at least one extracted data features in the plurality of extracted data features is selected from the group consisting of bed exit procedure, sit-to-stand time, gait, duration of bed occupancy, whether the human being is undergoing intravenous therapy, and whether the human being is using an assisting device.

In another embodiment of the system, the method steps are performed after: at least one sensor in the plurality of sensors detecting the human being attempting to exit a bed in which the human being is resting; wherein the computer-executable program instructions, when executed by the microprocessor, further cause the central server to perform the step of receiving from the at least one sensor an indication of the detected attempt of the human being to exit the bed.

In another embodiment of the system, the system further comprises: an electronic medical records database communicatively coupled to the central computer server; wherein said computer-executable program instructions, when executed by said microprocessor, further cause said central server to perform the step of identifying in the electronic medical records database an electronic medical record for the human being, the identifying based at least in part on the extracted data features; in the determining step, the central server system determining the fall risk for the human being further based at least in part on medical information about the human being in the identified electronic medical record.

In another embodiment of the system, the computer-executable program instructions, when executed by the microprocessor, further cause the central server to perform the steps of: storing on the non-transitory computer-readable medium a data record of the plurality extracted features and the determined fall risk; receiving at the central server system from the plurality of sensors additional data about the human being gathered by the plurality of sensors; extracting from the received additional data about the human being a second plurality of data features; determining a second fall risk for the human being based at least in part on the second extracted data features, and at least in part on the extracted data features in the data record of the non-transitory computer-readable medium.

In another embodiment of the system, the system further comprises a monitoring, computer system communicatively coupled to the central computer server; wherein the computer-executable program instructions, when executed by the microprocessor, further cause the central server to perform the steps of transmitting to the monitoring computer system an indication of the determined fall risk.

DETAILED DESCRIPTION OF THE PREFERRED EMBODIMENT(S)

Figure 1:
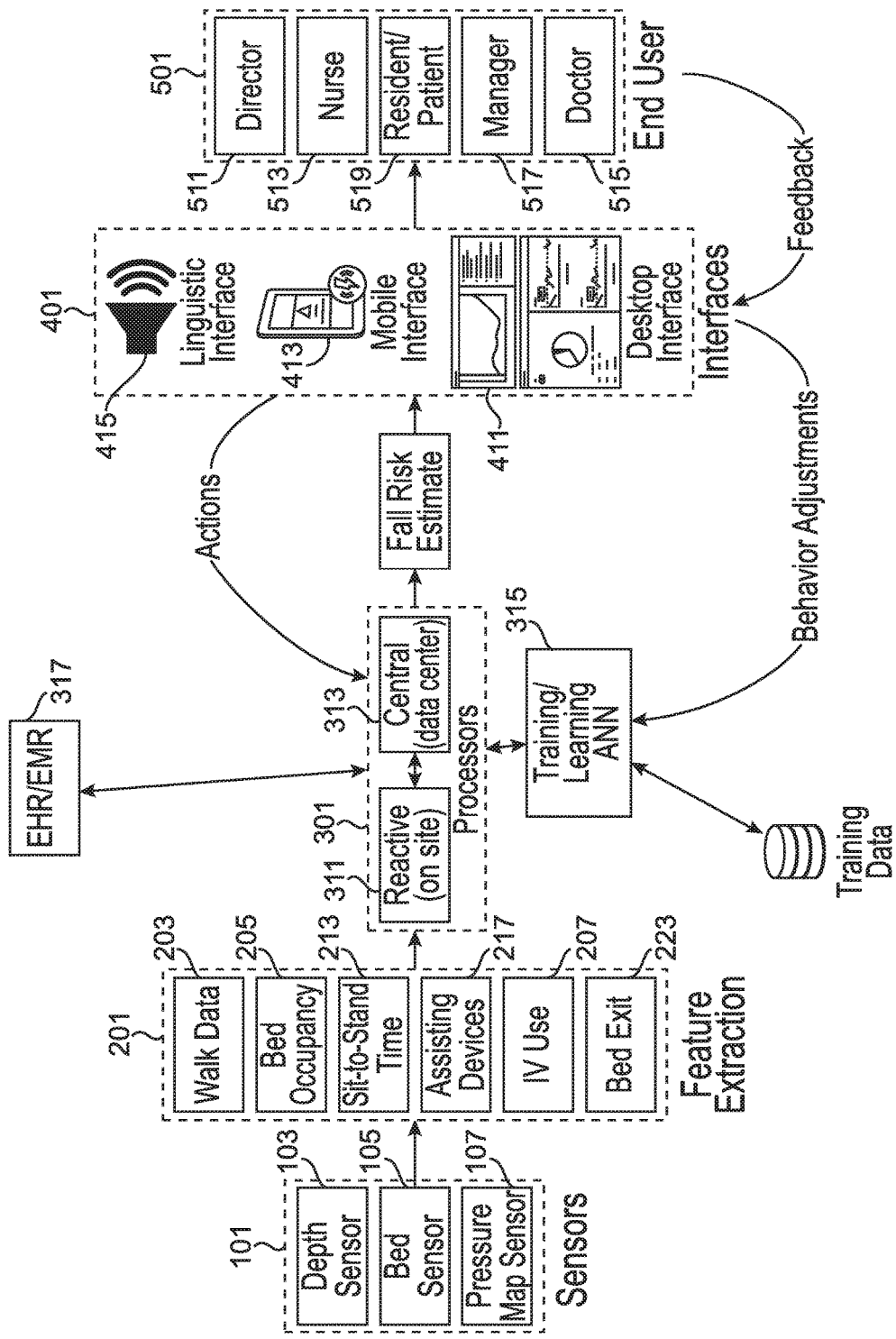
FIG. 1 provides a general block diagram of an embodiment of a system for assessing fall risk.

The following detailed description and disclosure illustrates by way of example and not by way of limitation. This description will clearly enable one skilled in the art to make and use the disclosed systems and methods, and describes several embodiments, adaptations, variations, alternatives and uses of the disclosed systems and methods. As various changes could be made in the above constructions without departing from the scope of the disclosures, it is intended that all matter contained in the description or shown in the accompanying drawings shall be interpreted as illustrative and not in a limiting sense.

Described herein, among other things, is a system and method for the automatic assessment of a person's fall risk. The systems and methods herein utilize a more objective standard and evaluation of a person's gait and stance and other factors to determine their current, and instantaneous, likelihood of a fall as well as their ongoing fall risk. Further the systems and methods used herein utilize machine observations and calculations so as to eliminate much of the potential bias or relative skill that is currently used in conjunction with human observations and evaluations.

The systems and methods described herein provide an automated system for the assessment of fall risk which generally provides a more accurate determination of a patient's instantaneous and long term fall risk, and which provide the calculation in a deidentified manner without tethering to the patient. The system discussed herein will generally utilize a variety of specific sensors in combination to evaluate a patient and to determine values indicative of certain indicators of fall risk and from that determine a general likelihood that the person will fall at some time during their stay in the institution. The system will generally determine two types of fall risk. This includes the person's instantaneous fall risk (which is the risk that the person will fall in short order given their current activity) as well as their long term fall risk (which is the risk that a person will suffer a fall at some time during their stay in the institution).

It should be recognized that assessing long term fall risk is different from predicting if an individual will or will not fall. In effect, an assessment of long term fall risk can be considered a placement of an individual into a tranche or other category where they are considered to have an increased or decreased statistical probability of suffering a fall within a determined period of time which generally corresponds to a window larger than the next few seconds, minutes, or other period where a fall is immediately imminent. Based on the assessment, the patients behavior, and allowed activity, may be limited while they are in the facility in order to control the risk.

This limitation, in turn, is, therefore, intended to alter the likelihood of the patient actually suffering a fall. For example, a patient which is seen as having a very high likelihood of falling during their stay may not be allowed to walk unaided at all while they are there, may be confined to a wheelchair, or may be confined to their bed. Even if this patient falling was a near certainty in the long term indicator, they now may not suffer a fall because they do not have the opportunity to fall.

Thus, systems such as the present one, in the prediction of long term fall risk, are intended to allow the institution using them to decrease the likelihood of falls for the patient population as a whole, but will not necessary increase or decrease the likelihood of falls from any one individual or group of individuals. It would not be surprising for the system to cause there to be reduced falls in a group most susceptible to falling in this calculation while an increase of falling incidents occurs in those less likely to fall. For example, a group with a reduced likelihood to fall may be provided with less restrictive behavior patterns, this can mean that they fall in conjunction with their expected rate. A more likely to fall group, however, may be restricted in such a way that they fall less than predicted because they are not given as much opportunity to fall.

Another important aspect of the present systems and methods is that they can also predict instantaneous fall risk. This is the fall risk that any patient will have because of what they are doing at any instant, regardless of what their general fall risk is. Often this is due to them having a current status or fall risk indicator which has changed from the normal. For example, a patient who is confined to their bed due to the effects of anesthesia wearing off, but who would otherwise have a very low long term fall risk, would likely have a very high instantaneous fall risk, if they are trying to get out of bed or are moving toward the bathroom. Similarly, a patient who is fairly stable when walking with a walker may have a very high fall risk if they were seen to be attempting to walk without it. This can be contrasted with a patient would have a very low instantaneous fall risk if they are sitting on a chair in their room, or are in their bed, even if they are very unstable on their feet.

Throughout this disclosure, certain terms will generally be considered to have certain meaning. While not limiting the definition of these terms as would be understood to one of ordinary skill, the following can assist in understanding the operation of the systems and methods.

The term "computer" as used herein describes hardware which generally implements functionality provided by digital computing technology, particularly computing functionality associated with microprocessors. The term "computer" is not intended to be limited to any specific type of computing device, but it is intended to be inclusive of all computational devices including, but not limited to: processing devices, microprocessors, personal computers, desktop computers, laptop computers, workstations, terminals, servers, clients, portable computers, handheld computers, smart phones, tablet computers, mobile devices, server farms, hardware appliances, minicomputers, mainframe computers, video game consoles, handheld video game products, and wearable computing devices including but not limited to eyewear, wristwear, pendants, and clip-on devices.

As used herein, a "computer" is necessarily an abstraction of the functionality provided by a single computer device outfitted with the hardware and accessories typical of computers in a particular role. By way of example and not limitation, the term "computer" in reference to a laptop computer would be understood by one of ordinary skill in the art to include the functionality provided by pointer-based input devices, such as a mouse or track pad, whereas the term "computer" used in reference to an enterprise-class server would be understood by one of ordinary skill in the art to include the functionality provided by redundant systems, such as RAID drives and dual power supplies.

It is also well known to those of ordinary skill in the art that the functionality of a single computer may be distributed across a number of individual machines. This distribution may be functional, as where specific machines perform specific tasks; or, balanced, as where each machine is capable of performing most or all functions of any other machine and is assigned tasks based on its available resources at a point in time. Thus, the term "computer" as used herein, can refer to a single, standalone, self-contained device or to a plurality of machines working together or independently, including without limitation: a network server farm, "cloud" computing system, software-as-a-service, or other distributed or collaborative computer networks.

Those of ordinary skill in the art also appreciate that some devices which are not conventionally thought of as "computers" nevertheless exhibit the characteristics of a "computer" in certain contexts. Where such a device is performing the functions of a "computer" as described herein, the term "computer" includes such devices to that extent. Devices of this type include but are not limited to: network hardware, print servers, file servers, NAS and SAN, load balancers, and any other hardware capable of interacting with the systems and methods described herein in the matter of a conventional "computer."

For purposes of this disclosure, there will also be significant discussion of a special type of computer referred to as a "mobile device". A mobile device may be, but is not limited to, a smart phone, tablet PC, c-reader, or any other type of mobile computer. Generally speaking, the mobile device is network-enabled and communicating with a server system providing services over a telecommunication or other infrastructure network. A mobile device is essentially a mobile computer, but one which is commonly not associated with any particular location, is also commonly carried on a user's person, and usually is in constant communication with a network.

Throughout this disclosure, the term "software" refers to code objects, program logic, command structures, data structures and definitions, source code, executable and/or binary files, machine code, object code, compiled libraries, implementations, algorithms, libraries, or any instruction or set of instructions capable of being executed by a computer processor, or capable of being converted into a form capable of being executed by a computer processor, including without limitation virtual processors, or by the use of run-time environments, virtual machines, and/or interpreters. Those of ordinary skill in the art recognize that software can be wired or embedded into hardware, including without limitation onto a microchip, and still be considered "software" within the meaning of this disclosure. For purposes of this disclosure, software includes without limitation: instructions stored or storable in RAM, ROM, flash memory BIOS, CMOS, mother and daughter board circuitry, hardware controllers, USB controllers or hosts, peripheral devices and controllers, video cards, audio controllers, network cards, Bluetooth® and other wireless communication devices, virtual memory, storage devices and associated controllers, firmware, and device drivers. The systems and methods described here are contemplated to use computers and computer software typically stored in a computer- or machine-readable storage medium or memory.

Throughout this disclosure, terms used herein to describe or reference media holding software, including without limitation terms such as "media," "storage media," and "memory," may include or exclude transitory media such as signals and carrier waves.

Throughout this disclosure, the term "network" generally refers to a voice, data, or other telecommunications network over which computers communicate with each other. The term "server" generally refers to a computer providing a service over a network, and a "client" generally refers to a computer accessing or using a service provided by a server over a network. Those having ordinary skill in the art will appreciate that the terms "server" and "client" may refer to hardware, software, and/or a combination of hardware and software, depending on context. Those having ordinary skill in the art will further appreciate that the terms "server" and "client" may refer to endpoints of a network communication or network connection, including but not necessarily limited to a network socket connection. Those having ordinary skill in the art will further appreciate that a "server" may comprise a plurality of software and/or hardware servers delivering a service or set of services. Those having ordinary skill in the art will further appreciate that the term "host" may in noun form, refer to an endpoint of a network communication or network (e.g. "a remote host"), or may, in verb form, refer to a server providing a service over a network. ("hosts a website"), or an access point for a service over a network.

Throughout this disclosure, the term "real-time" generally refers to software performance and/or response time within operational deadlines that are effectively generally contemporaneous with a reference event in the ordinary user perception of the passage of time for a particular operational context. Those of ordinary skill in the art understand that "real-time" does not necessarily mean a system performs or responds immediately or instantaneously. For example, those having ordinary skill in the art understand that, where the operational context is a graphical user interface, "real-time" normally implies a response time of about one second of actual time for at least some manner of response from the system, with milliseconds or microseconds being preferable. However, those having ordinary skill in the art also understand that, under other operational contexts, a system operating in "real-time" may exhibit delays longer than one second, such as where network operations are involved which may include multiple devices and/or additional processing on a particular device or between devices, or multiple point-to-point round-trips for data exchange among devices. Those of ordinary skill in the art will further understand the distinction between "real-time" performance by a computer system as compared to "real-time" performance by a human or plurality of humans. Performance of certain methods or functions in real-time may be impossible for a human, but possible for a computer. Even where a human or plurality of humans could eventually produce the same or similar output as a computerized system, the amount of time required would render the output worthless or irrelevant because the time required is longer than how long a consumer of the output would wait for the output, or because the number and/or complexity of the calculations, the commercial value of the output would be exceeded by the cost of producing it.

The present system is generally designed to provide information to a user which will allow a user to act on it in a certain proscribed manner so as to, hopefully, reduce a risk of injury from fall. A risk assessment can generally not prevent or inhibit a fall and it will generally be accepted that a certain number of patients will still fall in an institution in accordance with statistical likelihood. However, it is generally a goal of the present systems and methods to allow for the number of falls, and their potential severity, to be reduced overall (e.g. in a statistically significant way). At the same time, the systems can also generally inhibit the need to overly restrict behavior to inhibit falls. Those with low falling risk (e.g. not statistically significantly greater than would be the case if they were not in the institution, or not statistically significantly greater than the population as a whole) can be allowed freedom of movement.

By identifying more accurately those at risk to fall versus those that are not, able-bodied individuals can be provided with increased freedom within a health care setting (and generally improved quality of life) while those with an increased risk can be provided with additional resources to inhibit the likelihood of them actually suffering a fall event. In an extreme case, an individual with an extremely high fall risk can be confined in a particular environment where the chance of a fall, or an injury from a fall, is dramatically reduced.

Further, because the system allows for determination of both long term and instantaneous fall risk, falls and high risk occurrences can also generally be quickly detected, and responded to in real-time or near real-time, and particularly unique situations can create quick reactions to inhibit falls. Accurate assessment of fall risk can enable health care professionals to proactively intervene and potentially prevent falls before they occur, while still allowing for generally increased freedom of motion for most of the patient population.

As discussed herein, the system and methods generally create a fall risk assessment of a patient in a hospital setting, a resident in a senior living community, or a person in a home setting. That is, they operate within a controlled environment and as such relate to predicting the likelihood of a fall while the patient is within that environment. While this is not required and any setting can utilize the systems and methods, these settings generally provide concerns for increased fall risk.

The fall risk assessment systems and methods are generally produced by a computer system (10) such as that shown in the embodiment of FIG. 1. The system (10) comprises a computer network which includes a central server system (301) serving information to a number of clients (401) which can be accessed by users (501). The users are generally humans who are capable of reacting to the provided fall risk assessment as part of their job or task description. Thus, the users will commonly be medical personal (511), (513), or (515), corporate officers or risk management personnel (517) associated with the environment being monitored, or even the patient themselves or family members or guardians (519).

In order to perform the risk assessment, the server (301) will take in a variety of information from a plurality of sensors (101) which will provide various indications of the person's current actions. From those sensors' (101) output, a variety of characteristics of the patient's fall risk (201) can be determined. These characteristics may then be processed by the server (301) to produce an instantaneous fall risk assessment. This can then be combined with historical data for this patient (313) and/or data from a general population to which the patient is associated, to determine their long term fall risk as well as to indicate any unique factors for this patient which may give a better indication of instantaneous fall risk. This is commonly done through some form of learning software (315) as the system can operate in the form of a feedback loop.

An important aspect of the risk assessment system (10) is that none of the sensors (101) are tethered to the patient. That is that the patient does not need to wear any sensor or comply with any protocol for the risk to be assessed. This allows for the system (10) to be institutional and to monitor any, and generally all, patients in the facility environment at all times. It also allows for the system (10) to not require the patient to be setup on the system (10) in order for it to begin monitoring. Instead, monitoring can be of any individual as soon as they are present in the facility.

An advantage of a non-tethered system (10) is that the fall risk assessment is generally compliant with the Health Insurance Portability and Accountability Act (HIPAA although often abbreviated HIPPA). Specifically, the system (10) does not require access to or use protected health information in order to determine an instantaneous fall risk. It also operates in real-time or near real-time, operates continuously within the environment and generally does not require human intervention. The system (10) can accurately and quickly, often in real-time, assess an instantaneous fall risk of any individual it can observe. Further, buy untethering the system, the fall risk can be stored for patient data which is readily connected by the server (301) to a patient and used over time without need to connect the information with any tethering object.

Often times connection of data to the patient in a deidentified way is through the use of non-digital data in conjunction with the digital data. For example, digital data can identify a patient via an unconnectable number or other identifier which has no connection to the actual person and is not connectable with the person from the digital data. However, the machine can provide information to human personnel that the person (identified as X123 to the machine) in room 23 needs assistance and they know that person is John Doe because that's the only person in the room. This is an example where the digital data is effectively totally deidentified (and theft or access provides data which is generally not connectable with any real person), but data can be connected to an individual in appropriate settings.

While it is not required, in the embodiment of FIG. 1, the determination of fall risk is based on 6 different criteria values or features (201) which are assessed through a variety of different sensors (101). These criteria (201) generally relate to various indicators of how stable a person is, as well as indications of certain current criteria which indicate instantaneous scenarios that can potentially effect fall risk. In the embodiment of FIG. 1, these criteria (201) are generally as follows.

The first element is an individual's sit to stand time (213). Generally, this determination looks at how long it takes an individual to use from a sitting position to a standing position. A longer calculation will generally indicate an increased fall risk as it indicates that the person is potentially rising unsteadily, or lacks leg strength. The second criteria is the individual's typical walking speed and gait (203). An individual walking faster and more confidently will generally be at a reduced fall risk to one who shuffles or moves unsteadily. A third criteria can relate to an individual carrying out a bed exit (223) with no corresponding walk. Generally, someone who is trying to get out of bed is doing so because they wish to go somewhere else. How a person moves as they exit their bed can be indicative of their ability to walk.

A further criterion which is to be examined is the length of bed occupancy which is also tied to the frequency of exit (205). A person who has spent long periods of time in bed will likely have an increased fall risk. However, one who regularly gets up may also have an increased fall risk as they are simply more exposed to the possibility of falls. A final variable is the patient's connection or exposure to stability inhibiting (207) or assisting (217) objects. Most commonly, on an inhibition side would be connection to an IV bag (207) or other object which can hinder standard motion or assisting device. These can show that a person is forced to carry out more complicated walking actions in order to move which increases fall risk. For example, being tethered to an IV bag provides an individual with a ready support device (although not a particularly good one) but also requires them to concentrate and move the IV support while they are walking which makes walking much more complicated. On the alternative side if a patient is using an assistive device (217) such as a cane or walker, while this may indicate that the person has a generally increased long term fall risk, their short term fall risk is usually decreased as the device's purpose is specifically to inhibit falls.

In all cases, the readings in these criteria (201) are generally processed through a machine learning algorithm (315) and compared with data (313) compiled over a number of years. The system server (301) can determine when the particular values are being obtained for an individual it has evaluated before (and therefore provide results based on that particular individual) but can also assess the data for macro patterns within groups or the population of individuals (e.g. for males over the age of 65 who have had hip replacements). This generally results in a fall risk assessment of each individual which is generally more accurate than other currently used fall risk assessment tools.

FIG. 1 provides an overview of how the analysis will generally work. The first element is the sensor array (101) which is used to monitor the individual. In order to untether the individual from the system, these sensors (101) will generally be remote from the individual (e.g. not located on their person or carried by them). Instead, they are generally located in areas where the person is likely to be. The first, and generally primary, sensor is a camera (103) for capturing depth image data.

In an embodiment, this camera (103) will comprise a camera which takes video or similar image over time data and the capturing of depth image data. This data will generally be used to provide for gait information (203) such as is discussed in U.S. patent application Ser. No. 13/871,816, the entire disclosure of which is herein incorporated by reference. In order to provide for increased privacy, the depth camera may utilize silhouette processing as discussed in U.S. patent application Ser. No. 12/791,496, the entire disclosure of which is herein incorporated by reference, or may utilize recording optics for recording the patient in an electromagnetic spectrum outside of human vision. That is, the camera, in an embodiment, may record in the infra-red or ultra-violet portions of the spectrum.

Infra-red cameras are particularly of value because the human body naturally emits heat which emission is visible in the infra-red spectrum. However, the infra-red image of any patient, even when converted into a spectrum visible to the human eye, is generally extremely difficult for a user to connect with any individual who may be monitored. The human eye cannot naturally view that patient's infra-red emissions and the images appear to be different. As such, an infra-red camera can allow for video to be taken of an individual which is effectively deidentified from the individual as a human viewing the video is generally unable to connect the infra-red image to a particular individual they have seen in the visible light spectrum. Further, like X-ray systems utilized in airports, viewing of a human being in the infrared spectrum generally obscures personal details and results in an image which is generally not seen as revealing or embarrassing.

The infrared image of each individual, is however, generally unique and, in an embodiment, a machine can interlink the infra-red image, upon it being detected, to a patient based upon such similarity. The video system (103) is primarily used to watch the patient while they are in motion and may be placed in rooms, common areas, hallways, dining facilities, or other areas that the patient may go. As the system (103) generally does not produce a video which contains any private or identifying information, such systems can be posted even in areas of relative privacy such as bathrooms and sleeping areas.

The camera (103) will generally utilize the video to search for patterns in motion that can be indicative of fall risk. Specifically, the camera image will generally be processed to provide for a variety of the elements and variables used in the fall risk computation. Specifically, the camera can be used for spatial and temporal parameters (those that change over time or space) such as the patient's gait (203), sit-to-stand time (213), and bed exit (223) patterns. All of these elements of data change both temporally (as the patient moves over time) and often spatially (as they move across the camera's (103) field of view).

While gait (203) is often one of the more valuable indicators for determining long term fall risk, a concern is that most human's gaits are somewhat individual and while general patterns in gait can lead to indications of long term fall risk, it is the case that this particular variable can be less valuable for determination of instantaneous fall risk unless the gait is directly indicative of a fall occurring at that instant (e.g. it shows that the person just tripped).

For instantaneous determinations, elements that do not relate specifically to the act of locomotion, but to the preparation of locomotion before it commences, can be particularly valuable. The depth camera (103) can also analyze the type of motion the patient engages in when exiting a bed (223) or when standing from a sitting position (213). This analysis can often give a much quicker indication of an instantaneous fall risk based upon the person's immediate returns. For example, a patient may be groggy when they rise and that grogginess can slow them down, and make them hesitate (to overcome a potential feeling of dizziness or nausea) when they are upright. These indicators can provide an immediate indicator that regardless of the person's long term fall risk, their instantaneous risk is heightened and they may require immediate assistance.

In settings where a bed is associated with the patient (either because they have residential facilities at the location or because they are at least at some point in time lying down on a bed assigned to them as is common in a hospital) a bed sensor (105) and/or pressure map sensor (107) may be used to detect when the bed is occupied (205), when the patient exits the bed (223), and the actions they take to attempt their bed exit (223). Bed sensors (105) and pressure map sensors (107) can, in an embodiment, be of the type described in U.S. patent application Ser. No. 13/600,539, the entire disclosure of which is herein incorporated by reference. These types of sensors can provide details both that a patient is getting out of bed and about how they are getting out of bed. They can also be attached to other objects that a patient may lie or sit on such as, but not limited to, a chair, couch, or cushion as use of these objects, like a bed, generally indicate that a patient is not currently attempting locomotion.

Bed sensor (105) and pressure sensor (107) information can be used to determine if the patient is exhibiting a particular type of weakness (e.g. they appear to be moving a leg with their hand as opposed to moving it under its own power) which can indicate increased or decreased fall risk, as well as simply determining that the person is attempting to rise versus simply rolling over. It is an important aspect of the system to recognize that a patient that is lying down or sitting generally has a very low instantaneous fall risk. Falls generally occur from standing, and, thus, one value of the system is to detect that a person is not currently standing or walking, dramatically lowering their instantaneous risk.

Another concern in the system (10) is making sure that the data, which is deidentified form the patient, and is collected from them in an untethered fashion, is correctly connected with the patient. Depending on the setting (acute care, senior living, home), various computational algorithms may be used to separate data that belongs to the patient (e.g. the person who the bed "belongs" to) from data that belongs to other people in the field of evaluation which may be in common areas with the patient. This can include other patients, doctors, nurses, visitors, or cleaning staff, among others. Often these separation algorithms will work on data from the camera (101) attempting to separate one person's image from another. However, it is well-known that computer image recognition can have errors and one of the primary benefits of a bed sensor (105) is that it can provide additional data to connect a patient to their record.

The bed sensor (105) can be used to determine if a bed is occupied (205) (which is a likely indicator that the individual is not subject to a current fall risk as they are lying down) and can also be used to determine specifics of the person's bed exit (223) behavior. It can also be used when parameters obtained from the depth image data (103) and bed sensor (105) relating to the patient are generally combined and processed together. For example, a patient who is known to have arrived in their room on a bed (e.g. from surgery) is clearly the patient in the bed when the room is first occupied. When an individual on the bed is later detected to be attempting to exit the bed, it is also highly likely that this is the patient and the fact that the patient is getting up can be used as a cue to access other relevant data about this patient in real-time. Thus, the bed sensor (105) data, while providing specifics both that the patient is attempting to get up and how they are attempting to get up, can also be used as a double check, or primary indicator, to identify the patient as a particular patient in the system (10) and access their records (313).

The final criteria (201) of assisting (217) and inhibiting (207) device use can be obtained either from entered records which are accessed when the patient is identified (e.g. that a doctor has indicated that the patient is currently connected to an IV or an initial check in screening indicated that the patient walks with a walker) or can be obtained from image data. For example, a patient attempting to rise may be detected and data (313) loaded from the patient indicates that they walk with a walker. The image data may be scrutinized for an object that appears to be of the correct shape to that of a walker being near the point they are attempting to rise. Similarly, a bar of metal being detected as obscuring a patient's legs at the point one would expect the seat of a walker to be located would indicate that they are putting their legs down inside their walker.

The fall risk assessment is preferably generated automatically and continuously from the collected data at the processor (301), does not require patients to wear any device or otherwise be encumbered, and does not require human intervention beyond initially installing (and, when needed, maintaining) the sensors (101).

The processor (301) will typically first obtain and process information related to a particular patient's instantaneous fall risk. For example, if a patient is detected as attempting to leave bed, the system (10) will generally immediately begin evaluating their fall risk based upon their bed exit (223) procedure as well as a their sit to stand time (213). These two criteria may alone provide for accurate real-time risk indicator (311) even if the specific patient has not yet been identified and data (313) has not been loaded. The processor (301), however, will generally utilize the information it has stored in memory (313) to attempt to look up historical information (313) on the same patient. In a simple example, a patient attempting to get up from a bed generally got onto the bed previously. The system can therefore look up who the last patient was that was detected to lay down on the bed (or to whom the bed is associated) and determine if this appears to be the same patient. It may also locate electronic medical records (317) of the patient connected with the room to obtain other information. To the extent that the current patient can be associated with a prior record (313) and/or (317), the information about the patient's prior lone term fall risk can be factored into the current assessment of instantaneous fall risk. Further, the new information can be added back to the memory (313) to provide for additional historical data for use in the future. This type of feedback loop will often take the form of a training or learning algorithm (315).

Once the instantaneous or long term fall risk has been evaluated, the risk can be presented to a user (501) through a variety of interfaces (401). In a hospital setting, for example, the instantaneous fall risk, of a patient (and that the patient is currently attempting to get out of bed) may be provided to a nurse's monitoring station (411) for a floor or wing of a hospital in real-time or near real-time to allow them to quickly respond to a potentially high risk, situation being detected. This allows the nurses to know that a patient is active and, in the event they are determined to be a higher fall risk, may need nursing or other staff to go assist them in a very short time frame.

The system can also provide feedback to mobile devices (413), such the smartphone of a patient's doctor who may not be currently at a computer but wants updated information on the patient as they may need to follow up with the patient once they have reached a certain level of activity. Similarly, information may be provided to a patient directly. For example, if a patient is attempting to get out of bed that has been determined to have a higher fall risk, the system may activate a speaker (415) in the patient's room notifying them that the should stay in bed and that a nurse is on their way to assist them. This type of direct communication can potentially stop or hinder the patient from actually getting into a position where they may suffer a fall by slowing their attempt to get up, or stopping it. Long term fall risk data can be provided at the same types of interfaces to potentially allow for a nurse to quickly evaluate the nature of the current instantaneous risk (for example if it was a patient who had been moved to the room prior to them coming on shift).

As should be apparent from the above, much of the data on fall risk is obtained from as depth capturing camera (103). While this can be performed a variety of ways, in an embodiment the camera will capture an image and the processor will obtain the image, in real-time or near real-time from the camera and begin to process the images. Initially, foreground objects, represented as a three dimensional (3D) point cloud (a set of points in three dimensional space), can be identified from the depth image data using a dynamic background subtraction technique followed by projection of the depth data to 3D. A tracking algorithm can then be used to track foreground objects over time (generating a path history). Walking sequences can then be identified from the path history of a tracked object by identifying sections of the history during which the object's movement net a set of criteria such as maintaining a minimum speed for at least a minimum duration and covering at least a minimum distance. Such walking sequences can then be processed to generate temporal and spatial gait parameters, including walking speed, average speed, peak speed, stride time, stride length, and height, among others. As indicated above, U.S. patent application Ser. Nos. 12/791,496 and 13/871,816 provide examples of how depth image information may be processed to provide gait and other stability information.

Likewise, sit-to-stand motions can be identified using a camera (103) from the path history of tracked objects by identifying segments of the path history where the foreground object's height increased to a certain degree from its previous height after having been reduced to some degree from its previous height for a certain period of time. Depending on the setting (acute care, senior living, home), other contextual information, such as chair or bed locations, may be used to help segment sit-to-stand motions from the path history data. Finally, whether a patient is tethered to an IV or assisting device (such as a walker) may be determined using features (such as shape) extracted from the 3D point cloud representation of the foreground object as it is moving through the field of evaluation or may be associated based on entered information of a doctor.

For example, if the doctor indicated that this patient had an IV attached, the system will know to attempt to locate one in the image data. It can also quickly evaluate, once the device is located, how the patient is instantaneously interacting with it. For example, if a patient has been identified as having an IV bag, but they are exiting the bed on the side of the bed away from the bag, this can result in a very high instantaneous fall risk as the person can be badly encumbered by the IV they have apparently forgotten about.

Depending on the setting, computational algorithms may be used to separate data derived from the depth camera (103) that belongs to the patient from data that belongs to other people in the field of evaluation in order to improve the fall risk assessment. For example, in hospital settings where a bed sensor (105) is present, knowledge of when the bed was occupied and exited may be used to determine if an identified walking sequence belonged to the patient as opposed to someone else in the room. Specifically, if a walk occurred when the bed sensor (105) indicated the bed was occupied, it can be assumed it was not the patient walking and that data may be discarded as not of interest or may be attached to a different individual. However, if a walking sequence is identified while the bed is not occupied and the tracked object from whose history the walking sequence was identified is later located near or in the bed when the bed sensor (105) indicates the bed became occupied it can be assumed it was the patient getting in bed. Likewise, if the bed sensor (105) indicates a bed exit (223), and a walking sequence is later identified (while the bed is still unoccupied) from the path history of an object which was located in or near the bed at the time (or prior to) the bed exit being detected, it can be assumed it is the patient walking.

In senior living or other home settings, identification of clusters in the collected depth image data may be used to separate data that belongs to the patient from data that belongs to other people. For example, the height, average speed, stride time, and stride length parameters extracted from walking sequences during the previous 10 days might be used, in conjunction with a clustering algorithm (such as Gaussian mixture modeling), to separate the walking sequences into different clusters, with each cluster corresponding to a different individual. Prior knowledge of the patient (such as their height and age), which may be obtained from EMR type data (317), may then be used to identify which cluster corresponds to the patient as opposed to family members, nurses, or janitorial staff. After determining this correspondence, the cluster may then be used as, or to generate, a statistical or probabilistic model of the patient. Similar techniques may be used to identify sit-to-stand motions likely belonging to the patient in the various settings particularly if combined with pressure sensor (107) values collected by a particular chair or other fixture.

Given, among others, data from identified walking sequences (203) belonging to the patient, data from sit-to-stand motions (213) belonging to the patient, data indicating if the patient was tethered to an IV (207) or using an assisting device (217), and bed occupancy (205) and bed exit (223) data, a computational algorithm is used to combine this information into a fall risk assessment. This computational algorithm varies somewhat depending on the setting (acute, senior, or home) that is being monitored as the nature of individuals in these types of facilities is different. Specifically, a patient in an acute (hospital) setting, is less likely to have substantial history unless they are in the hospital on a regular basis.

Thus, in this case the system (10) is often forced to rely more upon real time calculations for the patient based on macro information (e.g. that patients generally with this type of characteristics tend to fall more often) to generate instantaneous fall risk assessments and general long term assessments as opposed to having specifics about this patient providing better long term risk assessment. In a home or residence setting, however, the patient will generally be under observation by some part of the system a large portion of their current time. This means that individual data can become far more valuable than macro population data and long term risk assessments can become more valuable. It should be recognized that one primary value of long term risk assessment is if the system detects certain significant deviations from prior long term behavior, this can indicate major instantaneous fall risk risks, even if the changes might otherwise be considered of low value. For example, if the patient is known to be stable when walking with a walker, but is suddenly seen to not be using their walker, this can present a very high instantaneous risk assessment, even when this detection would be the norm for a patient who does not need or use a walker.

In order to better illustrate how the system (10) can work, the following provides a brief description of one possible approach in an acute care setting where a bed and bed sensor (105) an camera (103) are associated with the patient's room. Firstly, an algorithm, and processing metric from the hospital may be established. The algorithm will generally be based on previous data compiled over a number of years and existing published research studies as well as any specific information known about the hospital. For example, if the hospital caters to a particular type of patient (e.g. cancer patients or children) these factors may be used to limit population data to those with similar characteristics. Based on this evaluation, an importance weight is assigned to each type of data point (peak speed from a walking sequence, sit-to-stand time, etc.). For instance, peak speed from a walking sequence may receive twice the importance weight of a sit-to-stand time in some embodiments.

When possible and appropriate, previous data compiled over a number of years is used in conjunction with machine learning techniques (for example, neural networks) to transform new data points into a common unit of fall risk (such as Timed-Up-and-Go Time). While this is not necessary, it can allow the system (10) to utilize all data collected in continually refine the accuracy of the system (10). Thus, criteria (201) may be consolidated or broken down in ways specific to that institution.

When a new data point is captured for which a transformation to the common unit of fall risk is available, the data point is first transformed using this available transformation. An updated fall risk assessment is then generated by taking a weighted average of the current fall risk assessment for the patient and the new data point. The weighting the new data point receives in the average is based on the importance weight associated with its data type. The weighting the current fall risk assessment receives is based on the number of data points previously captured, how much time has elapsed since the previous data points were captured, and the type of the previously captured data points. For instance, if the current fall risk assessment is based only on points captured more than 16 hours ago, the weight the current fall risk assessment receives in the average may be relatively small and have little effect on a risk calculation. However, if the current fall risk assessment is based on 10 data points with high importance weights captured within the past 2 hours, the current fall risk assessment may receive a relatively large weight in the average compared to the new data point.

When a new data point is captured for which a transformation to the common unit of fall risk is not available, the data point may instead be used to increase or decrease the current fall risk assessment by a fixed or relative amount, or to set the fall risk assessment to a specific value. For example, if the new data point indicates the patient was detected using an assisting device or tethered to an IV, the current fall risk assessment may be updated to reflect the patient is currently at high risk. However, if the data point indicates the patient has been in bed for a long period of time (e.g. more than 8 hours) without walking, the current fall risk may simply be increased to reflect a moderate risk if it was previously below that level as long periods of sleeping can result in grogginess and increased risk upon awakening.

For the purposes of example, let us consider the example of a patient being admitted to a hospital in order to illustrate how fall risk assessment works in an initial scenario. First, the system (10) needs to identify that this is a new patient. This may be done one of two ways: a) by entering admission data into the system either manually or automatically via integration with electronic medical records (317) which would indicate that it is not a patient the system has encountered before or b) using an "intelligent admissions" algorithms which can identify that this patient (based on sensor (201) feedback data) is one that has not been seen before because the patient is not identified as one in the system. Once the patient is identified as new, the system installed in the patient's room can reset the existing fall risk assessment (of the previous patient) and start a new continuous assessment based on the new patient's data. Effectively, as soon as the patient is identified as new, data points can begin being collected about the patient. For example, if the patient is moving as they approach their room, or move about their room, this data can be recorded. Further, the system (10) can also take in objective or subjective fall risk criteria entered by admittance personnel. For example, if the patient is indicated to walk with a cane, the system can now to look for one and to evaluate the patients gait based upon the gait of people who walk with canes.

Fall risk assessment is based on data points or criteria (201) as described in the previous section. Such data points include: data from identified walking sequences belonging to the patient (203), data from sit-to-stand motions belonging to the patient (213), data indicating if the patient was tethered to an IV (207) or assisting device (217), and bed occupancy (205) and bed exit (223) data. The system (10) can identify which data belong to the patient and which are generated by others in the room based on monitoring bed exits (223) and bed entries as described previously.

As soon as the first data point is captured, a first instantaneous risk assessment may be assigned. The first data point could be among others: a lack of bed exits for a certain amount of time (which puts the patient at higher risk), a use of an assisting device to exit the bed, possible tethering to an IV, the sit-to-stand time the first time the patient exits the bed, the characteristics of their first walk, the characteristics of movement of a patient on the bed while trying to exit the bed or a combination of some of the above. The functions that determine the risk level based on the above data are derived from previous data compiled over a number of years and existing published research studies, in conjunction with machine learning techniques (for example, artificial neural networks).

When a subsequent data point is captured it either gets combined with previous data points using weighted functions when available and applicable to adjust the instantaneous fall risk assessment accordingly or the new data point is used to directly adjust the instantaneous fall risk assessment, or both. Still further, the risk assessments may now be the calculation of a long term risk assessment or patient history. In an example, each new data point may be immediately evaluated for a particularly high instantaneous fall risk scenario (e.g. if the person's bed exit (223) manner indicates the lack leg strength) and if this test is passed, the system may revert to using the new data point in ongoing data evaluation of the long term fall risk. The process depends on the nature of the subsequent data point and some embodiments were provided above. The weighted functions are derived from previous data compiled over a number of years as processed by machine learning techniques.

During the patient stay at the hospital, the above process repeats over and over as the system (10) continues to identify new data points. The fall risk assessment is therefore instantaneous (as each individual data point or short window of data points may be used to determine an instantaneous risk), continuous and automated. Further, the longer the individual remains in the hospital, and the more continuously they are monitored, the better the long term fall risk assessment can become. This is turn can better influence the determination of the instantaneous fall risk as the data becomes more and more specific to this patient's particular behavior and a learning algorithm can detect nuances to this patient's behavior.

This improvement over time can be true both for this patient, and for patients with similar characteristics, but which may be new to the system. The fall risk assessment is presented to a health care professional via an interface that could be implemented on a mobile device, on the depth sensor system present in the room itself, on a web application or other device. The assessment is then also untethered and wireless. Finally, since none of the data captured in order to construct the data points can be used to identify a patient, the fall risk assessment is de-identified preserving the patient's privacy.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method of assessing the risk of a human being falling, comprising:
   providing a central sever system;
   providing a plurality of sensors communicatively coupled to said central server system, none of said sensors being in physical contact with said human being at least one sensor in said plurality of sensors detecting that said human being attempting to exit a bed in which said human being is resting;
   receiving at said central server system from said plurality of sensors data about said detected attempt of said human being to exit said bed;
   said central server system extracting from said received data about said human being a plurality of data features including an indication of the human being's bed exit procedure and the human being's sit-to-stand time during said bed exit procedure;
   said central server system determining a fall risk for said human being based at least in part on said extracted data features.

2. The method of claim 1, wherein each sensor in said plurality of sensors is selected from the group consisting of: a depth sensor, a bed sensor, and a pressure map sensor.

3. The method of claim 2, wherein at least one sensor in said plurality of sensors is a depth sensor, and said depth sensor is an infrared camera.

4. The method of claim 1, further comprising:
   providing an electronic medical records database communicatively coupled to said central computer server;
   said central server system identifying in said electronic medical records database an electronic medical record for said human being, said identifying based at least in part on said extracted data features;
   in said determining step, said central server system determining said fall risk for said human being further based at least in part on medical information about said human being in said identified electronic medical record.

5. The method of claim 1, further comprising:
   said central server system causing to be stored a non-transitory computer-readable medium a data record of said plurality extracted features and said determined fall risk.

6. The method of claim 5, further comprising:
   receiving at said central server system from said plurality of sensors additional data about said human being gathered by said plurality of sensors;
   said central server system extracting from said received additional data about said human being a second plurality of data features;
   said central server system determining a second fall risk for said human being based at least in part on said second extracted data features, and at least in part on said extracted data features in said data record of said non-transitory computer-readable medium.

7. The method of claim 1, further comprising:
   providing a monitoring computer system communicatively coupled to said central computer server;
   said central computer server transmitting to said monitoring computer system an indication of said determined fall risk;
   said monitoring computer system displaying said transmitted indication of said determined fall risk.

8. The method of claim 7, wherein said monitoring computer system is a desktop computer system of a nurse station in a medical facility.

9. The method of claim 7, wherein said monitoring computer is a mobile device.

10. The method of claim 1, further comprising:
    if said determined fall risk is above a predefined threshold, said central computer server causing a fall risk alert to be provided to said human being.

11. A system for assessing the risk of a human being falling, comprising:
    a plurality of sensors, none of said sensors being in physical contact with said human being;
    a central sever system communicatively coupled to said plurality of sensors, said central server system comprising a microprocessor and a non-transitory computer-readable medium having computer-executable program instructions thereon which, when executed by said microprocessor, cause said central server to perform the steps of:
      receiving from said plurality of sensors data about said human being gathered by said plurality of sensors at least one sensor in said plurality of sensors detecting that said human being attempting to exit a bed in which said human being is resting and said data including data about said detected attempt of said human being to exit said bed;
      extracting from said received data about said human being a plurality of data features including an indication of the human being's bed exit procedure and the human being's sit-to-stand time during said bed exit procedure;
      determining a fall risk for said human being based at least in part on said extracted data features.

12. The system of claim 11, wherein each sensor in said plurality of sensors is selected from the group consisting of: a depth sensor, a bed sensor, and a pressure map sensor.

13. The system of claim 12, wherein at least one sensor in said plurality of sensors is a depth sensor, and said depth sensor is an infrared camera.

14. The system of claim 11, further comprising:
an electronic medical records database communicatively coupled to said central computer server;
wherein said computer-executable program instructions, when executed by said microprocessor, further cause said central server to perform the step of identifying in said electronic medical records database an electronic medical record for said human being, said identifying based at least in part on said extracted data features;
wherein in said determining step, said central server system determining said fall risk for said human being further based at least in part on medical information about said human being in said identified electronic medical record.

15. The system of claim 11, wherein said computer-executable program instructions, when executed by said microprocessor, further cause said central server to perform the steps of:
storing on said non-transitory computer-readable medium a data record of said plurality extracted features and said determined fall risk;
receiving at said central server system from said plurality of sensors additional data about said human being gathered by said plurality of sensors;
extracting from said received additional data about said human being a second plurality of data features;
determining a second fall risk for said human being based at least in part on said second extracted data features, and at least in part on said extracted data features in said data record of said non-transitory computer-readable medium.

16. The system of claim 11, further comprising
a monitoring computer system communicatively coupled to said central computer server;
wherein said computer-executable program instructions, when executed by said microprocessor, further cause said central server to perform the steps of transmitting to said monitoring computer system an indication of said determined fall risk.

* * * * *